United States Patent
Ruiter et al.

(10) Patent No.: US 8,626,455 B2
(45) Date of Patent: *Jan. 7, 2014

(54) PUMP TESTER

(75) Inventors: Karl A. Ruiter, Honolulu, HI (US);
Mirik Hovsepian, Sunland, CA (US)

(73) Assignee: Pronk Technologies, Inc., Sun Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/603,062

(22) Filed: Sep. 4, 2012

(65) Prior Publication Data

US 2012/0330573 A1 Dec. 27, 2012

Related U.S. Application Data

(60) Division of application No. 13/463,539, filed on May 3, 2012, which is a continuation of application No. 13/450,092, filed on Apr. 18, 2012, and a continuation of application No. 13/130,568, filed as application No. PCT/US2009/065994 on Nov. 25, 2009.

(60) Provisional application No. 61/118,378, filed on Nov. 26, 2008, provisional application No. 61/251,418, filed on Oct. 14, 2009.

(51) Int. Cl.
*G01F 1/00* (2006.01)

(52) U.S. Cl.
USPC ............................................. 702/45

(58) Field of Classification Search
USPC .................. 702/45; 73/861.05; 417/53
See application file for complete search history.

(56) References Cited

U.S. PATENT DOCUMENTS

| 2,817,237 | A |   | 12/1957 | Stevens |
| 3,422,667 | A | * | 1/1969 | Hrdina ........................ 73/53.01 |
| 4,565,500 | A | * | 1/1986 | Jeensalute et al. .............. 417/53 |
| 5,355,735 | A | * | 10/1994 | Miller et al. ............... 73/861.05 |
| 2011/0036143 | A1 |   | 2/2011 | Riley et al. |

FOREIGN PATENT DOCUMENTS

| JP | 58-146334 A | 8/1983 |
| JP | 04-155220 | 5/1992 |
| JP | 2007-064759 | 3/2007 |

OTHER PUBLICATIONS

Non-Final Office action for U.S. Appl. No. 13/450,092 mailed Nov. 30, 2012.
Requirement for Restriction/Election for U.S. Appl. No. 13/450,092 mailed Sep. 17, 2012.
Non-Final Office action for U.S. Appl. No. 13/603,117 mailed Jan. 28, 2013.
Non-Final Office action for U.S. Appl. No. 13/463,539 mailed Sep. 25, 2012.

(Continued)

*Primary Examiner* — Tung S Lau
*Assistant Examiner* — Xiuquin Sun
(74) *Attorney, Agent, or Firm* — Brooks Acordia IP Law, P.C.; Pejman Yedidsion; Christopher Weiss

(57) ABSTRACT

Methods and devices for testing medical pumps via tracking induced single or multiple bubble trajectories within a fluid flow conduit by detecting a periodic synchronization event, via inserted bubble tracking of a signal processor unit, and methods of synchronized corrections of fluid flow data estimates based on the periodic synchronization event, where the periodic synchronization event detecting comprises detecting one or more pushes of a pump and one or more pauses of a pump.

13 Claims, 8 Drawing Sheets

(56) References Cited

OTHER PUBLICATIONS

Requirement for Restriction/Election for U.S. Appl. No. 13/463,539 mailed Jul. 31, 2012.
International Search Report for Serial No. PCT/US2009/065994 mailed Jul. 14, 2010.
Final Office action for U.S. Appl. No. 13/603,117 mailed May 8, 2013.
Final Office action for U.S. Appl. No. 13/453,539 mailed Apr. 3, 2013.
Notice of Allowance for U.S. Appl. No. 13/603,117, mailed Jul. 12, 2013.
Final Office action for U.S. Appl. No. 13/450,092 mailed May 29, 2013.

* cited by examiner

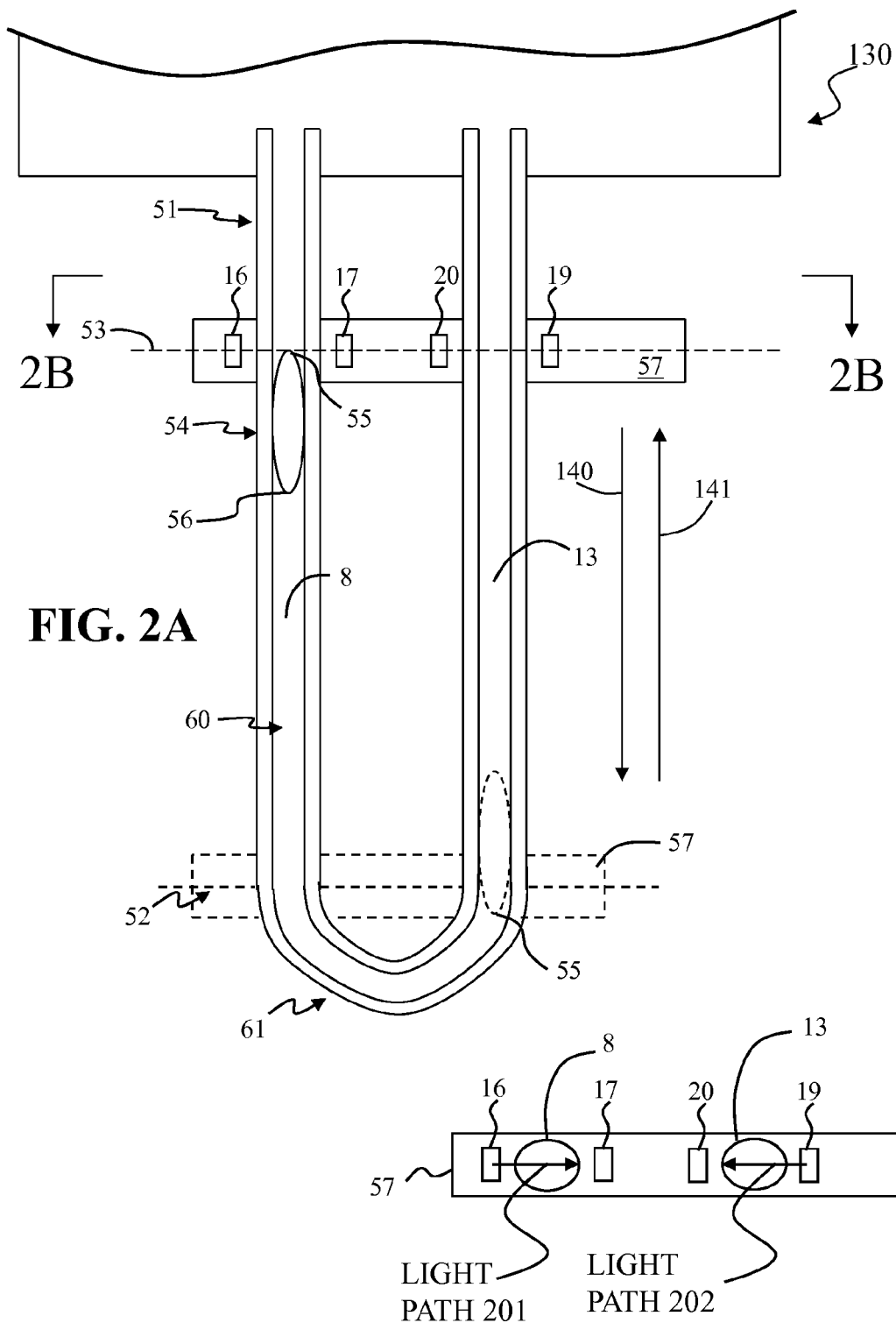

PUMP TESTER

CROSS-REFERENCE TO RELATED APPLICATIONS

This application is a divisional of U.S. patent application Ser. No. 13/463,539 filed May 3, 2012, and is a continuation of U.S. patent application Ser. No. 13/450,092, filed Apr. 18, 2012, and is a continuation of U.S. patent application Ser. No. 13/130,568, filed May 20, 2011, which is a U.S. National Stage Entry of PCT/US2009/065994, filed Nov. 25, 2009 which claims priority to and the benefit of U.S. Provisional Patent Application Ser. No. 61/118,378, filed Nov. 26, 2008 and U.S. Provisional Patent Application Ser. No. 61/251,418, filed Oct. 14, 2009, all of which are hereby incorporated by reference herein in their entirety for all purposes.

TECHNICAL FIELD

The present invention, in its several embodiments, comprises methods of, and devices for, testing fluid pumps, and particularly pertains to methods of, and devices for, testing medical pumps.

BACKGROUND ART

Modern medical practice utilizes a variety of fluid pumps for diverse applications such as introducing a saline solution into patients to maintain hydration and supplying patient controlled anesthesia. Because of the variety of applications for these pumps, they employ widely different flow rates ranging from a fraction of a milliliter per hour to several liters/hour. Presently devices which measure the flow and volume output of pumps do so by passing the pump fluidic output into a transparent tube and introducing bubbles into the tube. Measurements of flow and volumetric output may be derived by measuring the time required for the bubbles to move past multiple fixed optical sensors. Devices embodying such means of flow measurement are of limited utility for timely measurements because, at low flow rates, a derived flow measurement may require several minutes, several hours, or may require several tens of hours for the bubbles under test to move between points along an array of multiple fixed optical sensors.

DISCLOSURE OF INVENTION

The invention, in its several embodiments, may include an exemplary method of fluid flow rate estimation of a pump comprising: (a) detecting a periodic synchronization event, via inserted bubble tracking of a signal processor unit comprising a central processing unit and addressable memory; and (b) synchronizing, based on the periodic synchronization event, either: (i) a flow characteristic calculation, i.e., a determination of a flow characteristic value; or (b) a flow characteristic data display; or (c) both. The signal processor unit may include circuitry and/or a central processing unit and addressable memory. A periodic synchronization event detecting of the exemplary method may comprise: (a) detecting one or more pushes of a pump based on a time-interval and at least one of: a carriage position change and carriage motion; and (b) detecting one or more pauses of a pump based on time-interval, a threshold, and at least one of: a carriage position change and carriage motion. A synchronizing of a flow characteristic calculation based on the periodic synchronization event may comprise: (a) collecting flow data through each push-pause cycle of the pump; and (b) adding, by the signal processing unit, the collected flow data to an average value when a pause is detected following a push detection. An example of the inserted bubble tracking of the method claim may comprise: (a) inserting a first bubble into the fluid flow; and (b) tracking, by the signal processor unit, a travel of at least one of: the leading edge of the inserted first bubble and the trailing edge of the inserted first bubble, the tracking based on photo-detector output of a first photo-detector disposed on a controlled, translatable carriage.

The invention, in its several embodiments, may also include an exemplary pump tester comprising: (a) a light-transmissive fluid conduit comprising an outflow path and an inflow path relative to a manifold configured for bubble insertion; (b) a carriage translatably disposed along at least one of: the outflow path of the conduit and the inflow path of the conduit, where the carriage includes a first light emitting unit and a first photo-receptor; (c) a motor having linkage configured to translate the carriage; and (d) a signal processing unit comprising at least one of: (i) a circuit and (ii) a microprocessor comprising a central processor and addressable memory; the signal processor configured to output motor command signals based on input signals from the first photo-receptor. The linkage of a pump tester may comprise a belt engaging a guide pulley and a drive pulley driven by a motor, wherein the translatable carriage is attached to the belt. The signal processing unit of a pump tester may be further configured, e.g., via circuitry and/or a central processor executing instructions, to: (1) detect, via inserted bubble tracking, one or more pushes of a pump based on a time-interval of carriage motion; (2) detect one or more pauses of a pump based on time-interval of carriage motion less than a threshold; (3) collect flow data through each push-pause cycle of the pump; and (4) add, by a signal processing unit, the collected flow data to an average value when a pause is detected following a push detection.

Embodiments of the present invention include methods of determining and/or measuring fluid flow of a pump via a pump tester having a light-transmissive fluid conduit, where the steps may comprise: (a) inserting a first bubble into the fluid flow; and (b) tracking, by a signal processor unit, the travel of at least one of: the leading edge of the inserted first bubble and the trailing edge of the inserted first bubble, the tracking based on photo-detector output of a first photo-detector disposed on a controlled, translatable carriage. The signal processor unit used to practice the exemplary methods may comprise a central processing unit and addressable memory. An exemplary method may further comprise inserting a second bubble into the fluid flow; and tracking, by a signal processor unit, the travel of at least one of: the leading edge of the inserted second bubble and the trailing edge of the inserted second bubble, the tracking based on at least one of: photo-detector output of the first photo-detector disposed and a second photo-detector, disposed on the controlled, translatable carriage.

Another exemplary method embodiment of the present invention may comprise: (a) providing a translatable carriage having at least one carriage-mounted light-emitter, the carriage disposed about a fluid conduit, the fluid conduit extending from a manifold; (b) inserting a bubble into a fluid of the fluid conduit, the fluid having a flow rate and a direction of flow within the fluid conduit; (c) testing for at least one of: a leading edge and a trailing edge of the bubble, the testing based on a change in received light from the carriage-mounted light-emitter; (d) if the at least one of: a leading edge and a trailing edge of the bubble, is detected, then (i) determining a first carriage position via the carriage-mounted light-emitter, e.g., a topmost carriage position of a vertically mounted pump tester, and (ii) advancing the carriage in the direction of flow to a carriage stopping position, e.g., a bottommost carriage position of a vertically mounted pump tester, (e) returning the carriage in a reverse direction of flow, i.e., in a direction from the stopping position toward the first carriage position; (f) testing for at least one of: a leading edge and a trailing edge of the bubble, the testing based on a change in received light from the carriage-mounted light-emitter; (g) if the at least one of: a leading edge and a trailing edge of the bubble, is detected, then (i) determining a second carriage position, and (ii) invoking a tracking mode based on a difference between the second carriage position, the first carriage position, and the carriage stopping position; and (h) if the at least one of: a leading edge and a trailing edge of the bubble, is not detected, then invoking a first tracking mode. The fluid conduit of the exemplary method may comprise a return portion configured to return the fluid to the manifold, and the first tracking mode may comprise returning the carriage to the first carriage position, and detecting at least one of: a leading edge and a trailing edge of the bubble. If the determined second carriage position is less than one-tenth of a distance between the stopping position and the first carriage position, then the exemplary method may invoke a second tracking mode, where the second tracking mode may comprise detecting a leading edge of the bubble, and slewing the carriage to maintain detection of at least one of the leading edge of the bubble. If the determined second carriage position is less than one-half of a distance between the stopping position and the first carriage position and greater than one-tenth of a distance between the stopping position and the first carriage position, then the exemplary method may invoke a third tracking mode, where the third tracking mode comprises: detecting a trailing edge of the bubble; and slewing the carriage to maintain detection of the trailing edge of the bubble. If the determined second carriage position is greater than one-half of a distance between the stopping position, then invoking a fourth tracking mode, where the fourth tracking mode may comprise: detecting at least one of: a leading edge and a trailing edge of the bubble, slewing the carriage to the stopping position, and detecting at least one of: a leading edge and a trailing edge of the bubble. Another exemplary method embodiment of the present invention may comprise a method of measuring fluid flow by (a) inserting a first bubble into a flow of fluid of a light-transmissive conduit, the conduit having a first portion and a second portion; (b) tracking, by a signal processor unit, the travel of the inserted first bubble in the first portion of the conduit, the tracking based on photo-detector output of a first photo-detector disposed on a controlled, translatable carriage, whereby the second photo-detector may be receiving light emitting diode emissions via the first portion of the conduit; (d) inserting a second bubble into the flow of fluid; (e) detecting the inserted second bubble, based on photo-detector output of the first photo-detector disposed on the controlled, translatable carriage; (f) tracking, by the signal processor unit, the travel of the inserted second bubble, the tracking based on the photo-detector output of the first photo-detector disposed on the controlled, translatable carriage; (g) detecting the inserted first bubble, based on photo-detector output of the second photo-detector disposed on the controlled, translatable carriage, whereby the second photo-detector may be receiving light emitting diode emissions via the second portion of the conduit; and (h) tracking, by the signal processor unit, the travel of the inserted first bubble, the tracking based on the photo-detector output of the second photo-detector disposed on the controlled, translatable carriage.

BRIEF DESCRIPTION OF DRAWINGS

Embodiments of the present invention are illustrated by way of example and not limitation in the figures of the accompanying drawings, and in which:

FIGS. 2A and 2B depict, in a functional arrangement, features of the exemplary apparatus embodiment of FIGS. 1A and 1B;

BEST MODES FOR CARRYING OUT THE INVENTION

Figure 1A:
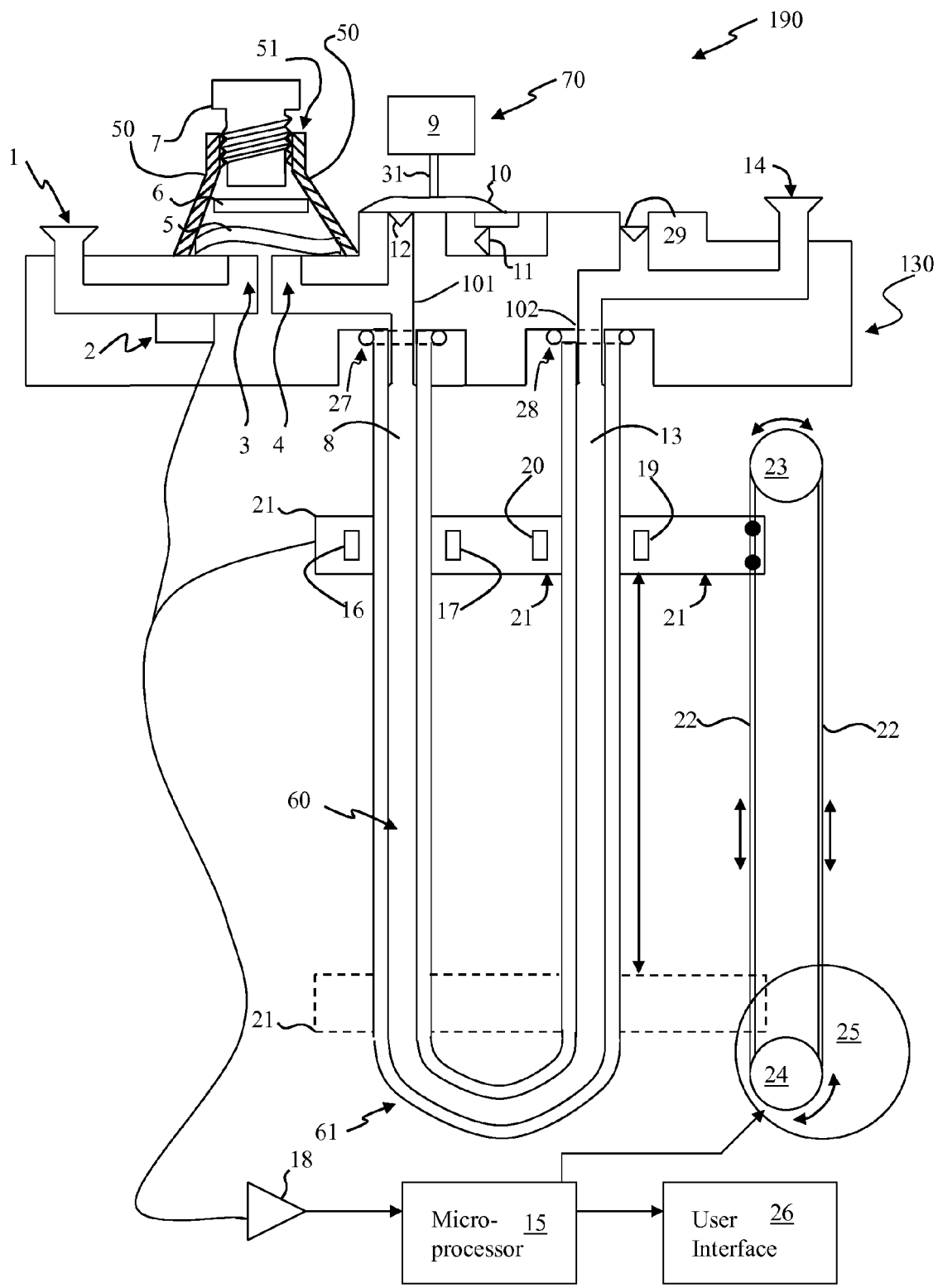
FIG. 1A depicts, in a functional arrangement, an exemplary apparatus embodiment of the present invention.
Figure 1B:
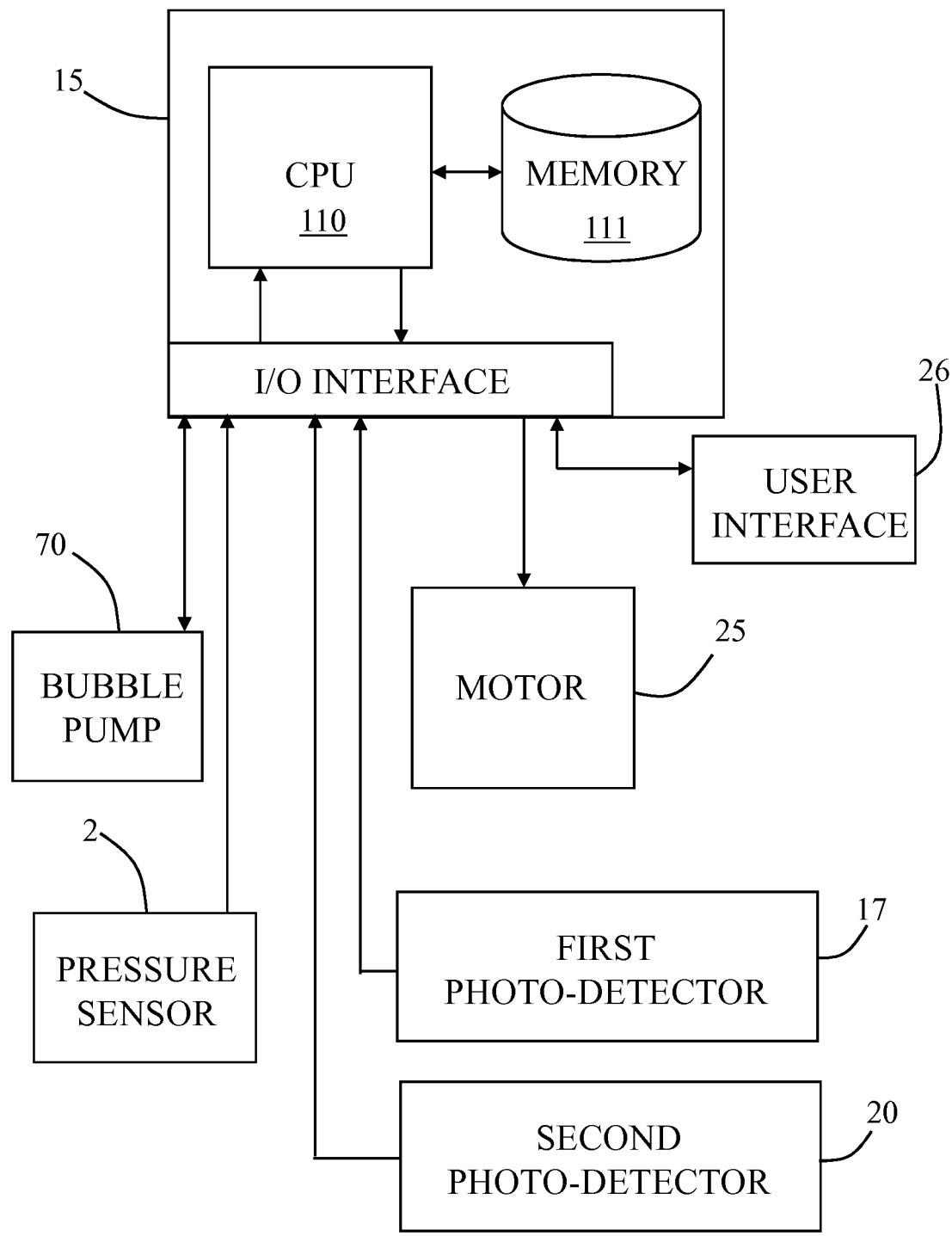
FIG. 1B depicts, in a functional block diagram, an exemplary apparatus embodiment of the present invention.

A schematic diagram of an exemplary device embodiment of the present invention is shown in FIGS. 1A and 1B. Fluid from the pump to be tested enters the device (190) though the inlet port (1). The fluid may then be ducted past a pressure sensor unit (2) that measures the pressure, and the pressure sensor unit (2) may include a sensor to measure the temperature of the fluid.

The fluid may then be ducted to the inlet port (3) of an occlusion valve (50), and may flow to the outlet port (4) of the occlusion valve (50) by displacing an elastomeric diaphragm (5). Deflection of the elastomeric diaphragm (5) may be opposed by pressure from a resilient foam rubber spring (6), in which pressure may be modified by adjusting a screw (7) engaging a threaded collar (51) of the occlusion valve (50). A pressure sensor may be placed proximate to the occlusion value and pressure sensors may be placed along the fluid conduit. Output, i.e., sensed pressure, may be transmitted to the signal processor, which may be a microprocessor (15).

Fluid passing through the occlusion valve (50) may then be ducted to an outbound and return fluid conduit assembly such as a U-shaped bubble tube (60). A bubble pump (70) having an actuator (9) may cause motion (e.g., via a mechanical connection (31)) of the bubble pump diaphragm (10), which may cause air to move through the bubble pump inlet valve (11) and then though the bubble pump outlet valve (12), and then into the bubble tube (60).

Fluid and bubbles may travel down the first leg (8) of the bubble tube (60) of the fluid conduit, around the bend (61) then up the second leg (13) of the bubble tube (60) of the fluid conduit, and the fluid and bubbles may then be ducted to the outlet port (14).

FIG. 1A shows a carriage (21) in side view. A carriage may have apertures through which the conduit (60) may pass. FIG. 2B shows an orthogonal view of the carriage (57) where a first LED (16) may emit a first light path (201) that may be detected at a first photo-detector (17) after passing through the first leg (8) of the conduit (60), and where a second LED (19) may emit a second light path (202) that may be detected at a second photo-detector (20) after passing through the second leg (13) of the conduit.

The presence of a bubble in the first leg (8) of the bubble tube (60) may be detected by a signal processing unit that may comprise circuitry and/or a microprocessor (15), having a central processing unit (110) and addressable memory (111), as seen in FIG. 1B, when there are changes in the amount of output light of a first light-emitting device such as a first light-emitting diode (LED) (16) that is received by a first photo-sensor (17) and as amplified by the amplifier circuit (18). The presence of a bubble in the second leg (13) of the bubble tube (60) may likewise be detected by the microprocessor (15) by utilizing a second light-emitting device such as a second LED (19) and a second photo-detector (20) to detect changes in received output light from the second LED (19) attributable to the presence of a bubble in the fluid stream.

The LEDs (16, 19) and photo-detectors (17, 20) may be affixed to a movable carriage (21) that may be affixed to a drive unit, e.g., a drive belt (22), and the movable carriage (21) may be moved under the control of the microprocessor (15) by utilizing pulleys (23 and 24) which may be driven by a stepper motor (25). For example, the stepper motor (25) may be under the control of the microprocessor (15) and the belt (22) may be driven by the drive pulley (24) engaged by the stepper motor (25).

As the fluid moves through the first and second legs of the bubble tubes (8, 13), bubbles may be introduced via the bubble pump (70), and the motion of the bubble may be tracked by photo-detectors on the carriage (21), a carriage that may be moved in various patterns under the control of the microprocessor (15). This allows the microprocessor (15), by executing computer-readable instructions, to measure the flow rate and volume delivered by the pump and to display that data along with the fluid temperature and pressure data on the display of a user interface (26).

The bubble tube (60) may be formed from a single glass tube that mates into the rest of the fluid ducting or manifold via O-rings (27 and 28) in such a manner, as shown in cross-section in FIG. 1A, that the bubble tube assembly may be easily pulled free from the rest of the fluid ducting (101, 102) for cleaning.

An anti-siphon valve (29) may be provided to preclude the effect of suction, i.e., a partial vacuum, that may be present in the tubing connected to the outlet port (14); a suction that may otherwise cause air to be drawn though the bubble pump valves (11,12).

In typical operation, bubbles and fluid travel down the first leg (8) of the bubble tube (60), and the carriage (21) may track the bubble, by translating with the bubble, until the bubble reaches the bend (61) in the tube. The carriage (21) may then pause in its translational motion proximate, in this example, to the bend (61) in the tube for the bubble to round the bend (61) and to travel into the second leg (13) of the tube (60) and then may track the bubble up the second leg of the tube (13). The steps of the stepper motor (25) may be made to be relatively small, e.g., smaller that the minimum possible spacing of multiple fixed photo detectors, the motion of the fluid may be tracked in fine resolution, and thereby allow for relatively precise flow and volume measurements that may be made rapidly, even at relatively low flow rates.

Due to the wide range of flow rates to be tested, multiple sets of computer-readable instructions may be required for tracking and measurement of bubble motion. Exemplary sets of computer-readable instructions are discussed below in conjunction with FIGS. 2A and 2B.

Sub-Process or Method 1: Ultra High Flow Rates

An exemplary first tracking method embodiment of the present invention may be embodied as an optional first sub-process, the carriage (57) may be placed at the topmost position (51) and a bubble (54) is introduced in the first leg (8) of the bubble tube (60). The carriage (57) may remain in position and the time interval—required for the bubble (54) to travel through the entire bubble tube (60) and be detected in the second leg (13) of the tube—is determined via measurements. If the bent portion (61) of the tube represents an unknown volume, there may be significant loss of accuracy. This potential inaccuracy may be automatically calibrated out, i.e., computationally accounted for, by positioning the carriage at a second position, P2, and measuring the total travel time. If the travel time at the top most position may be represented by $TT_{top\text{-}most}$, the travel time at the second position may be represented by $TT_{P2}$, and the difference in tube volume between the top most position and P2 may be represented by DeltaV, then it may be determined that the flow rate, R, is:

$$R = \text{Delta}V/(TT_{top\text{-}most} - TT_{P2}) \qquad [\text{Eq. 1}]$$

and an estimate of the total tube volume, $V_{total}$, may be generated, including the bent portion, at:

$$V_{total} = R * TT_{top\text{-}most} \qquad [\text{Eq. 2}]$$

$V_{total}$ may be stored and used for further flow calculations. This process may be preferred for all flow rates in which the average flow rate cannot be accommodated by the motor's maximum speed.

Sub-Process or Method 2: Very Low Flow Rates.

An exemplary second tracking method embodiment of the present invention may be embodied as an optional second sub-process, the carriage (57) may be moved initially to its topmost position (51). Once the leading edge (56) of the bubble (54) is detected, or first detected, by the optics (16, 17) on the carriage (57), bubble tracking and measurement may begin. The carriage (57) may be moved, e.g., by the belt (22), as required to keep the leading edge of the bubble at or proximate the centerline (53) of the carriage's optics, where the carriage (57) is translated in a direction (140) away from the manifold (130). Flow rate and volume calculations may be updated each time the carriage is moved. When the carriage gets to its bottommost position (52) it may be returned, e.g., translated in a direction (141) to its topmost position to begin the process again. At very low flow rates, the system may track the bubble by tracking the leading edge (56) of the bubble (54) as it may be many minutes or even tens of minutes between the time the leading edge (56) of the bubble (54) first appears to the optics and the time the trailing edge (55) first appears to the optics.

Sub-Process or Method 3: Intermediate Flow Rates

An exemplary third tracking method embodiment of the present invention may be embodied as an optional third sub-process, the carriage (57) may initially be moved toward its topmost position (51). After the leading edge (56) of the bubble (54) is detected, or first detected, by the optics on the carriage, the carriage may remain in position until the trailing edge (55) of the bubble appears (FIG. 2A). Once the trailing edge (55) is detected, bubble-tracking and measurement taking may begin. The carriage may be moved in a direction (140) away from the manifold (130) as required to keep the trailing edge of the bubble (55) at the centerline (53) of the carriage's optics. Flow rate and volume calculations may be updated each time the carriage is moved. When the carriage reaches its bottom most position (52) it may pause in its translational motion until the bubble reappears in the second leg (13) of the bubble tube (60), and it then may track the bubble (54), e.g., according to its trailing edge (55), back up to the top most position (51) in a direction (141) toward the manifold (130) using, for example, the stepper motor (25) and belt (22) of FIG. 1A. At intermediate flow rates the system may more accurately track the trailing edge (55) of the bubble (54) because there may be micro-bubbles or foam present in the tube ahead (i.e., below on the first leg, above on the second leg, if the device is oriented vertically) of the bubble. These micro-bubbles collect on the leading edge of the bubble, causing it to grow and accordingly may potentially cause overestimation of the flow rate.

Sub-Process or Method 4: High Flow Rates

An exemplary fourth method embodiment of the present invention may be embodied as an optional fourth sub-process, the carriage (57) may initially be moved to its topmost position (51). After the leading edge (56) of the bubble (54) is first detected by the optics on the carriage, the carriage may be moved at a relatively high speed or full speed (or slew rate) to then stop at its bottom most position (52). When the leading edge of the bubble (56) is detected at its bottommost position (52) flow rate and volume calculations may be updated based on the amount of elapsed time, e.g., the time increment required, for the bubble to travel from the top most position (51) to the bottom most position (52). The carriage may remain in position until the bubble reappears in the second leg of the bubble tube (13) and the process may be repeated in that tube. When the average flow rate is over about one-half of the maximum flow rate that may be supported by the maximum speed of the stepper motor, this exemplary fourth method may be a preferred method where several pumps, when placed in operation, may not produce a steady flow, but rather may produce a flow that surges, practicably instantaneously, above and below the average value. When the instantaneous flow rate surges above the motor's maximum speed, it may become impracticable for the carriage to instantaneously track the bubble; but the average rate, as represented by the top most position (51) to bottom most position (52) travel time, may still be measured when the instantaneous flow rate surges above the motor's maximum speed. In practice, there may be negligible loss in accuracy when executing this fourth exemplary method, and at these relatively high flow rates, measurements may still be produced rapidly relative to the other tracking methods, or sub-processes, disclosed.

Method of Switching Tracking Method

Figure 3:
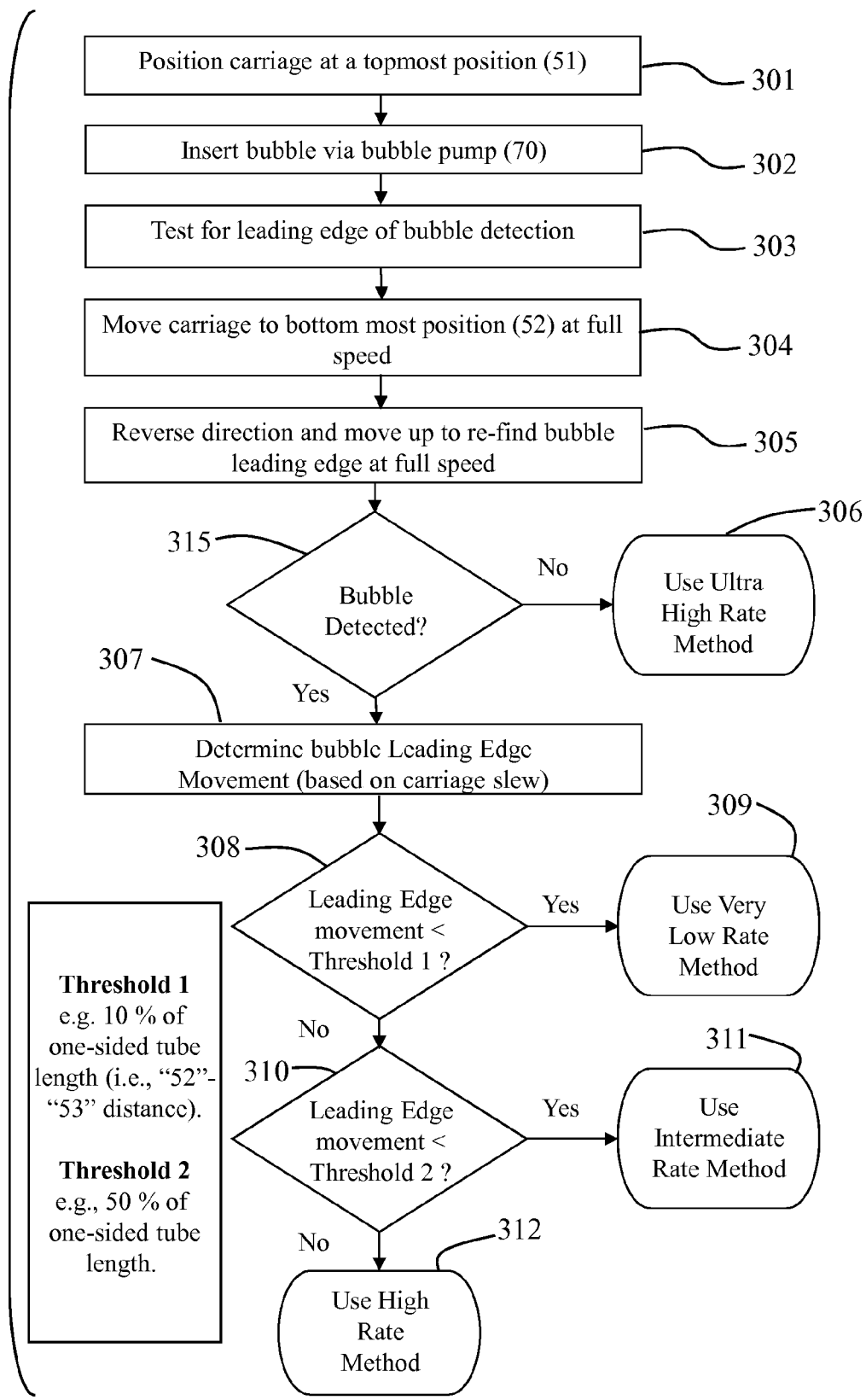
FIG. 3 is a top-level flowchart depicting a method embodiment of the present invention.

The various exemplary bubble tracking method embodiments, when selected, may be optimized for particular rates and for different rates. But, one may need to select the most accurate or quickest method of measure without advance knowledge of the rate. The method of switching tracking methods or optional tracking sub-processes, i.e., a method that provides for some or all of the methods as options, and provides for automated selection of tracking method (sub-process) is shown in the flowchart of FIG. 3. In some embodiments, the ultra high rate method may be termed the first tracking method, the very low rate method may be termed the second tracking method, the intermediate rate method may be termed the third tracking method, and the high rate method may be termed the fourth tracking method. The method of switching tracking methods (sub-processes) may be embodied as computer-readable instructions and executed via the microprocessor (15) of FIGS. 1A and 1B. Referring to FIG. 1A and FIG. 3, one may position the carriage (57) at a topmost position (51) (step 301). A bubble may be inserted into the tube via a bubble pump (70) (step 302). The microprocessor, executing computer-readable instructions, may test for a detection of a leading edge of the inserted bubble (step 303). The carriage (57) may then be moved to a bottom-most position (52) at full speed (step 304). Upon achieving the bottom-most position (52), the direction of travel of the carriage (57) may then be reversed and the microprocessor executing computer-readable instructions may test for a detection of the leading edge of the inserted bubble (step 305). If the leading edge of the bubble is not detected (test 315), then the microprocessor may invoke the ultra-high flow rate processing (step 306). If the leading edge of the bubble is detected (test 315), then the microprocessor may determine the bubble leading edge movement based on carriage slew (step 307). If the determined leading edge is less than a first threshold (test 308), e.g., ten percent of the one-sided tube length, i.e., first leg, tube length, then the microprocessor may execute the steps of the very low rate method (step 309). If the determined leading edge is greater than or equal to the first threshold (test 308) and less than a second threshold (test 310), e.g., 50 percent of the one-sided tube length, i.e., first leg, tube length, then the microprocessor may execute the steps of the intermediate flow rate method (step 311). If the determined leading edge is greater than or equal to the first threshold (test 308), and greater than or equal to the second threshold (test 310), then the microprocessor may execute the steps of the high rate method (step 312).

Multiple Bubble Embodiments

Some embodiments of the present invention may utilize multiple bubbles simultaneously. An exemplary embodiment for determining a volume measurement using two bubbles is shown in FIGS. 4A-4G.

Figure 4A:
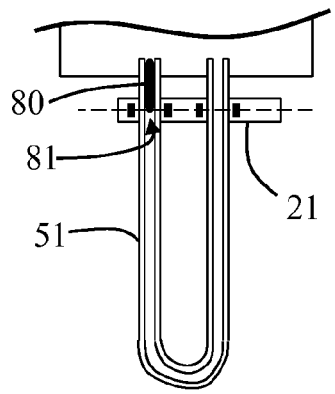
FIGS. 4A-4G each depict exemplary travel positions of a first induced bubble and/or second induced bubble of a two-bubble embodiment of the present invention.
Figure 4B:
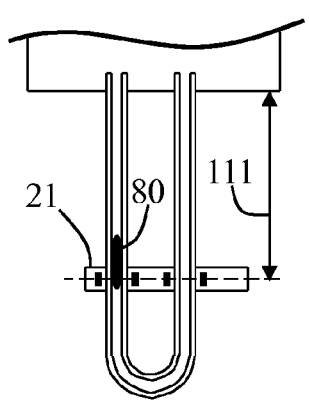
Figure 4C:
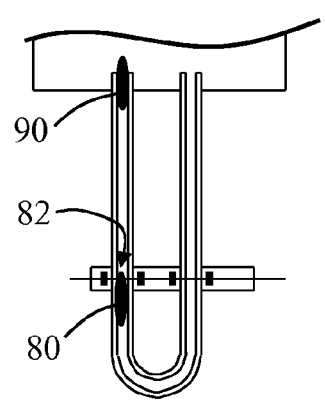
Figure 4D:
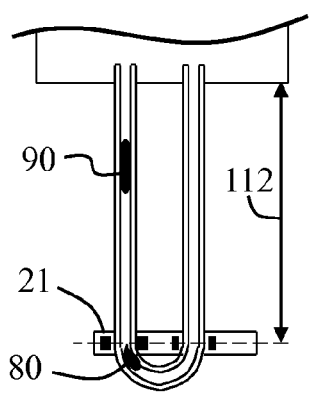
Figure 4E:
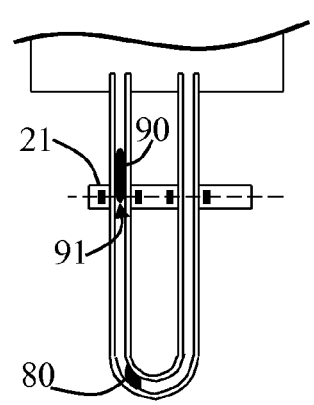
Figure 4F:
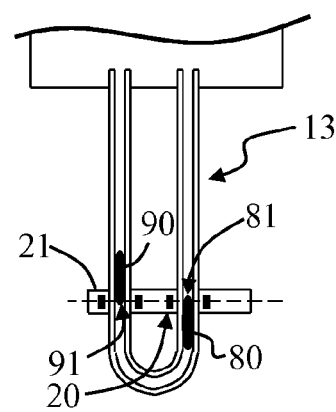
Figure 4G:
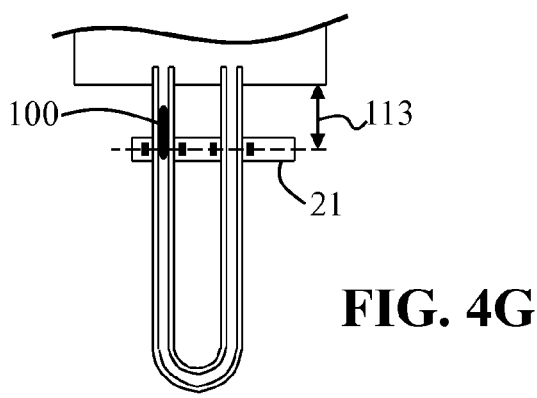

FIG. 4A shows a first bubble (80) introduced into the exemplary U-shaped tube (51) and the carriage (21) tracking the leading edge (81) of the first bubble (80). The leading edge tracking proceeds until the carriage (21) reaches a pre-determined location (111) as shown in FIG. 4B. Based on an event such as achieving a particular carriage location, e.g., drive belt travel or stepper motor increments, or based on a time difference, e.g., a bubble pump cycle, a second bubble (90) may be introduced to the exemplary U-shaped tube and the carriage switches to tracking the trailing edge (82) of the first bubble (80), as shown in FIG. 4C. The trailing edge (82) of the first bubble (80) is tracked until the carriage (21) reaches its bottom-most position (112), as depicted in FIG. 4D. From the bottom-most position, the carriage (21) is moved to the leading edge (91) of the second bubble (90) and the second bubble leading edge (91) is tracked as shown in FIG. 4E. The second bubble (90) leading edge (91) tracking continues until, as depicted in FIG. 4F, the leading edge (81) of the first bubble (80), having moved into the second leg (13) of the U-shaped tube, is detected by a second photo-detector (20) of the carriage (21). The leading edge (81) of the first bubble (80) or the leading edge (91) of the second bubble (90) may then be tracked up the second side (13) of the U-shaped tube until the carriage (21) reaches its upper most position (113) at which point a new first bubble (100) is introduced and the process repeats as depicted in FIG. 4G.

Synchronized Data Averaging

Figure 5A:
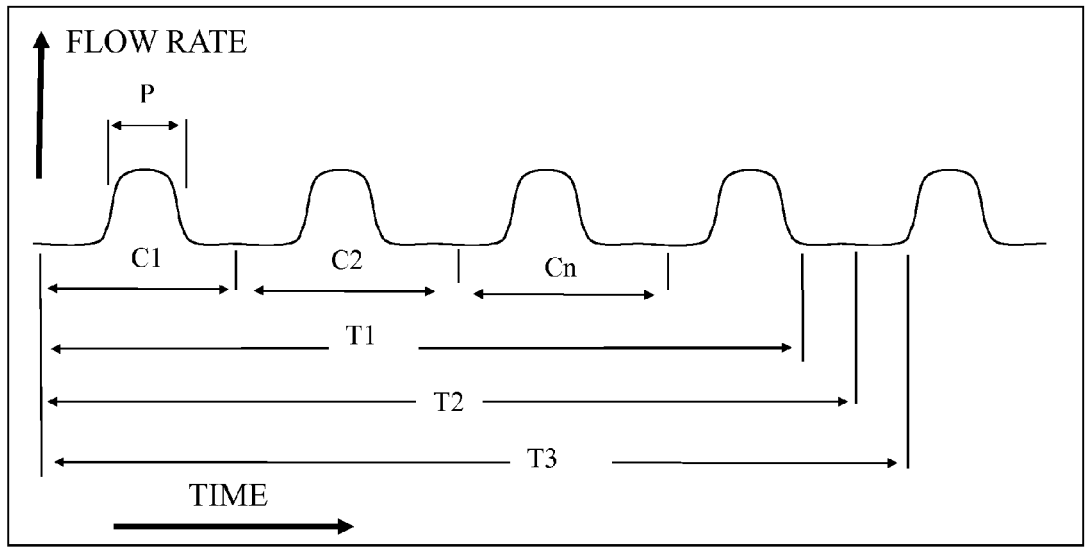
FIG. 5A depicts an exemplary pump cycle timeline.

Several medical pumps do not exhibit a steady, continuous flow. Rather, the flow exhibited is a periodic, pulsing flow. FIG. 5A shows the typical behavior of such a pump, with instantaneous flow plotted vs. time. The flow pattern consists of time periods in which the pump is pushing fluid of time P, and time periods where the pump is pausing of time C−P, in a total push+pause cycle time of C. Accordingly, FIG. 5A depicts an example of n+2 complete pump cycles. Typically the flow rate for such a pump is estimated as a continuously running average of the instantaneous flow rate. Whenever the running average contains anything other than an exactly even number of complete pump cycles it will be in error. For example, at the end of time interval T2 in FIG. 5A, the running average will show the correct average rate, but the end of time interval T1 is based on an erroneously high amount of push time and will provide for overestimate of the rate at the end of time interval T3 the average is based on an erroneously high amount of pause time and will provide for an underestimate of the rate.

If the true average rate is R, the worst case over-estimation, represented by R', is:

$$R'=R*C*(n+1)/(n*C+P) \quad [\text{Eq. 3}]$$

Where the "n" of equation number 3 above is the number of complete cycles in the average, C is the length of the total push pause cycle, and P is the length of the push part of the push pause cycle.

While the worst case underestimation, represented by R", is:

$$R''=R*(1/(1+(C-P)/n*C)) \quad [\text{Eq. 4}]$$

Figure 5B:
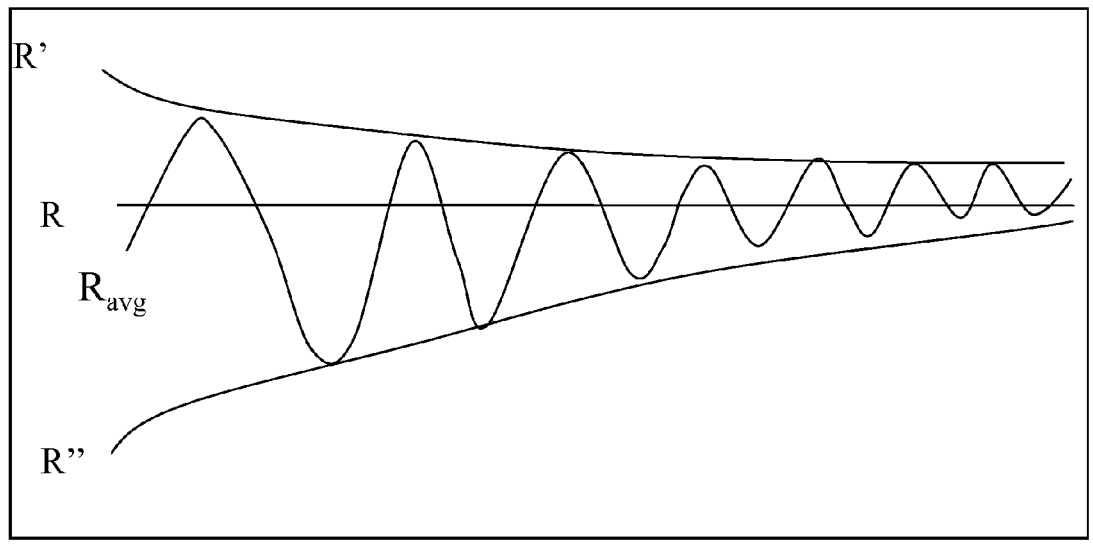
FIG. 5B depicts an exemplary running average timeline of an embodiment of the present invention.

FIG. 5B shows a cartoon of the running average, $R_{avg}$, oscillating between R' and R" and slowly converging on the presumed true average, R, and doing so as the number of complete cycles in the average, "n," increases.

Figure 6:
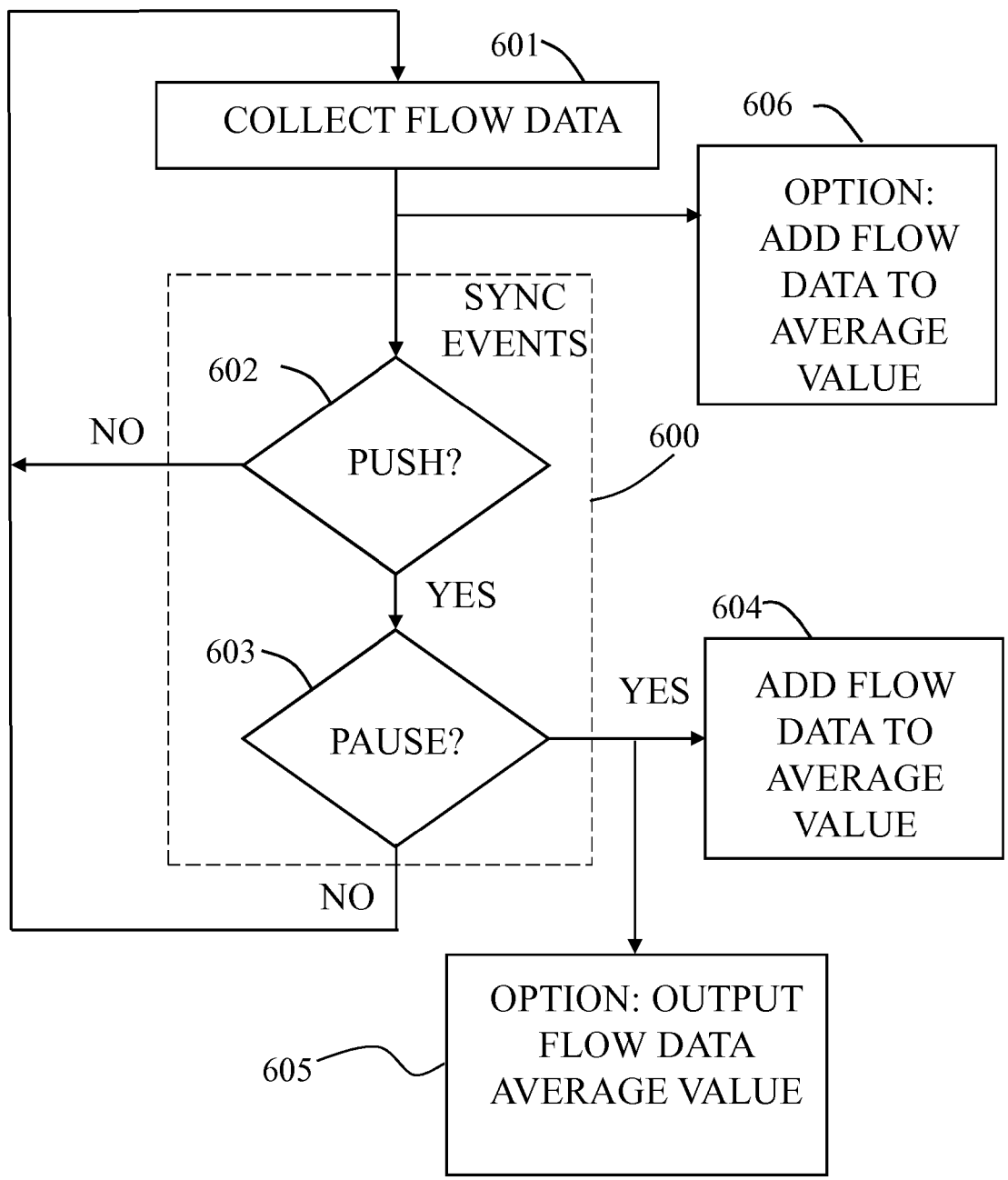
FIG. 6 is an exemplary top-level flowchart of an exemplary embodiment of the present invention.

In several applications, it may be desirable to measure flow rate to within a 1% error. For several pumps, a target error of less than 1% requires an "n" value of several hundred. This large number of cycles may require a total test length of several minutes to several hours, which may be impractical for time-constrained testing of a pumping device. Accordingly, a method embodiment of the present invention, depicted by the flowchart of FIG. 6, may provide for fluid flow rate estimation of a pump where the exemplary method comprises the steps of: (a) detecting a periodic synchronization event (600), via inserted bubble tracking of a signal processor unit comprising a central processing unit and addressable memory; and (b) synchronizing a flow characteristic calculation based on the periodic synchronization event. The signal processor unit may comprise circuitry and/or a central processing unit and addressable memory, where the central processor executes computer-readable instructions to execute the method. A periodic synchronization event (600) may be at a point or range along the push/pause cycle and may be tied to push/pause detection. An exemplary flow characteristic may be the average push volume per average time between pushes. For example, a synchronization event may be detected that indicates the present point or range in the push/pause cycle, e.g., the transition between the push time-region and the pause time-region, and sensor data, e.g., carriage location or rate information and/or fluid pressure in the conduit, may be input to the averaging process based on the detection of the synchronization event. In another example, the sensor data may be input in an averaging process at a sampling rate (606), but the result of the averaging process (605) may only be made available for output and/or display on the detection of a synchronization event. In another example, the flow characteristic may be expressed via a mathematical model representative of the average push length and a mathematical model representative of the average time between pushes, and the flow characteristic, as a pair of mathematical models, may be updated on the detection of a synchronization event.

Detections of periodic synchronization events may be based on time derivatives of carriage position changes, carriage linear velocity changes and/or may be based on changes in fluid pressure in the conduit or one or more time derivatives of fluid pressure changes in the conduit. An exemplary embodiment of the present invention may comprise the steps of a circuit and/or a microprocessor configured to: (a) detect pushes of a pump as a time of elevated and consistent carriage motion—reflective of bubble tracking; (b) detect pauses in the pumping as time-intervals where there is negligible carriage motion or where there is carriage motion less than some percentage of that detected during pushes; (c) collect measured and/or determined flow data through the push-pause cycle; and (d) add the collected flow data to an average value only when a pause is detected following a push detection. A microprocessor (15) of an exemplary embodiment of the present invention may execute computer-readable instructions for a test based on tracking leading or trailing portions of one or more induced bubbles according to an exemplary process depicted in the flowchart of FIG. 6 where the flow data is collected (step 601), a test may indicate that the pump is in a pause phase of a push-pause cycle (synchronization events 600), i.e., a pause is detected (test 603) following a push detection (test 602), and, if in a pause phase, then adding flow data to the average value (step 604). Embodiments of the exemplary detected pump pause-based method produce testwise acceptable flow rate numbers with "n" values in the range of two to ten.

In some cases optimal results may be achieved typically by combining the above exemplary synchronized averaging method with the multi-bubble application to a flow tube. In this combined embodiment, new bubbles are introduced and flow data are added to the average value only when a pause is detected following a push detection.

Figure 7:
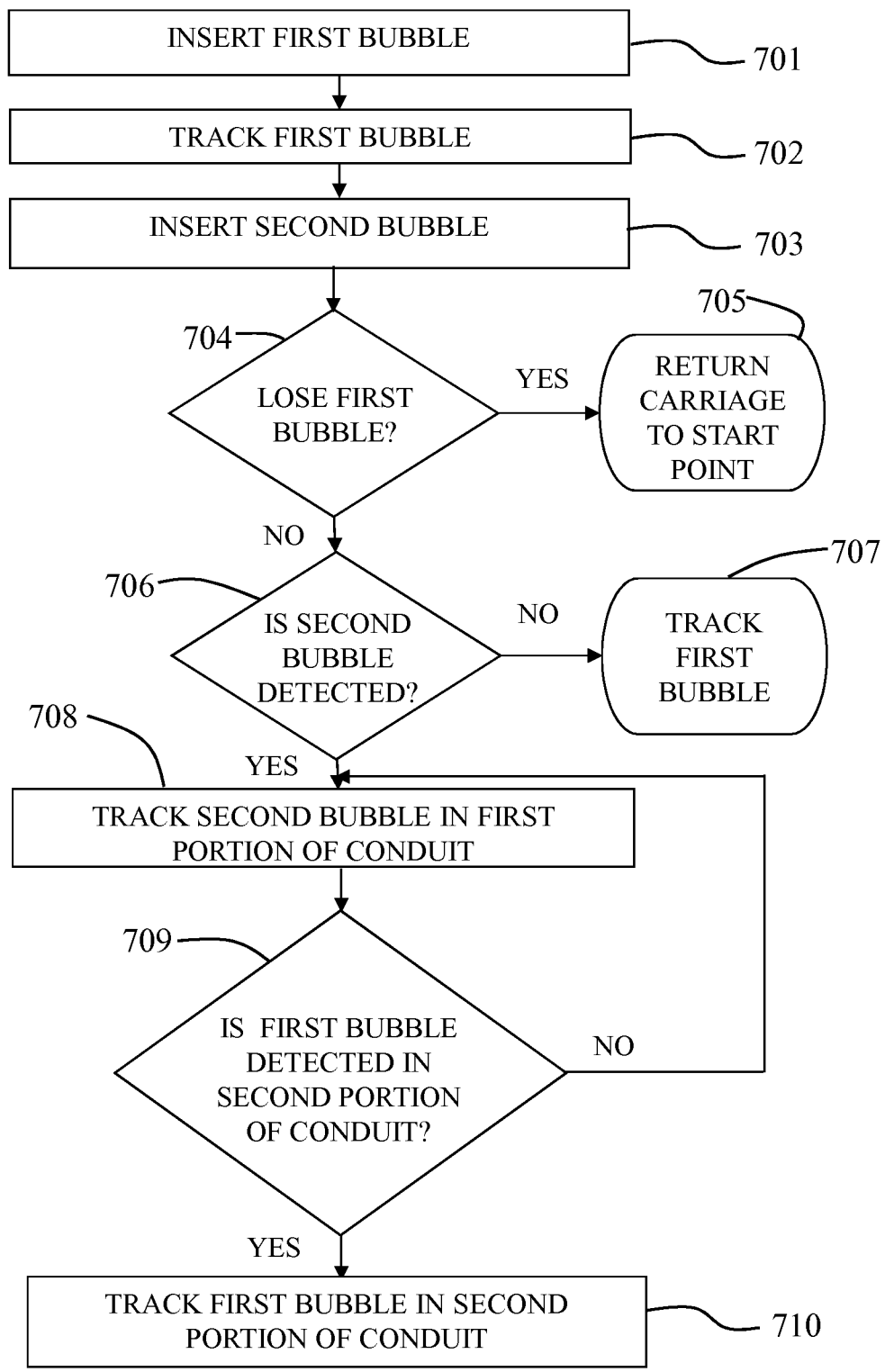
FIG. 7 is an exemplary top-level flowchart of an exemplary embodiment of the present invention.

FIG. 7 is a flowchart described with reference to FIGS. 4A-4G, where FIG. 7 is an example of the steps that may be executed by a computer executing computer-readable instructions to track a plurality of inserted bubbles in which a first bubble is inserted (step 701) into the first portion of the conduit and the first bubble is tracked (step 702), i.e., the carriage having a photo detector may be translated as the bubble moves based on received levels of carriage-based lights emissions. Then a second bubble is inserted (step 703) into the invention and a check is made as to the location of the first bubble (test 704). If the first bubble is lost, e.g., due to carriage travel limitations or a loss at tracking, the carriage returns to a starting point (step 705) and the process begins again for the next bubble. If the first bubble is not lost, then a check is made as to the location of the second bubble (test 706) and if the second bubble is lost, then the carriage gets moved back to the first bubble and it is tracked (step 707). If the second bubble is detected (test 706), then the second bubble is tracked in the first portion of the conduit (step 708), i.e., along the outflow direction. A check is then made to determine if the first bubble is detected in the second portion of the conduit (test 709), i.e., along the inflow direction. If the first bubble is determined to be in the second portion of the conduit, then the first bubble is tracked in the second portion of the conduit (step 710). If the first bubble is determined not to be in the second portion of the conduit (test 709), then the process returns to tracking, or continues to track, the second bubble in the first portion of the conduit (step 708). The process may be repeated for a plurality of bubbles.

It is contemplated that various combinations and/or subcombinations of the specific features and aspects of the above embodiments may be made and still fall within the scope of the invention. Accordingly, it should be understood that various features and aspects of the disclosed embodiments may be combined with or substituted for one another in order to form varying modes of the disclosed invention. Further it is intended that the scope of the present invention herein disclosed by way of examples should not be limited by the particular disclosed embodiments described above.

What is claimed is:

1. A method of fluid flow rate estimation of a pump comprising:
   detecting a periodic synchronization event, via inserted bubble tracking of a signal processor unit comprising a central processing unit and addressable memory, wherein the periodic synchronization event indicates at least one of: a present point in a push-pause cycle and a present range in a push-pause cycle; and
   synchronizing a flow characteristic determination based on the periodic synchronization event,
   wherein the periodic synchronization event detecting comprises:
      detecting one or more pushes of a pump based on a time-interval and at least one of: a carriage position change, a carriage motion, and a fluid pressure change; and
      detecting one or more pauses of a pump based on time-interval, a threshold, and at least one of: a carriage position change, a carriage motion, and a fluid pressure change;
      wherein the carriage motion during the detected one or more pushes of the pump is elevated and consistent during the time-interval, and the carriage motion during the detected one or more pauses of the pump is at least one of: a negligible motion and a set percent smaller than the carriage motion during the detected one or more pushes of the pump.

2. The method of claim 1 wherein the inserted bubble tracking comprises:
   inserting a first bubble into the fluid flow; and
   tracking, by the signal processor unit, a travel of at least one of: the leading edge of the inserted first bubble and the trailing edge of the inserted first bubble, the tracking based on received emission levels of a photo-detector output by a first photo-detector disposed on a controlled, translatable carriage, wherein the translatable carriage is configured to move in a translational motion relative to the fluid flow.

3. The method of claim 2 wherein the translational motion of the controlled, translatable carriage is effected by a stepper motor.

4. The method of claim 3 wherein the steps of the stepper motor are smaller than a minimum possible spacing of two or more fixed photo-detectors.

5. The method of claim 1 wherein the flow characteristic determination is output to a flow characteristic data display.

6. A method of fluid flow rate estimation of a pump comprising:
   detecting a periodic synchronization event, via inserted bubble tracking of a signal processor unit comprising a central processing unit and addressable memory, wherein the periodic synchronization event indicates at least one of: a present point in a push-pause cycle and a present range in a push-pause cycle; and
   synchronizing a flow characteristic determination based on the periodic synchronization event,
   wherein the periodic synchronization event detecting comprises:
      detecting one or more pushes of a pump based on a time-interval and at least one of: a carriage position change, a carriage motion, and a fluid pressure change; and
      detecting one or more pauses of a pump based on time-interval, a threshold, and at least one of: a carriage position change, a carriage motion, and a fluid pressure change;
      wherein the flow characteristic determination is expressed as a mathematical model representative of an average push length, and a mathematical model representative of an average time between the one or more pushes of the pump.

7. The method of claim 6 wherein the mathematical model representative of the average push length and the mathematical model representative of the average time between the one or more pushes of the pump are updated based on the detection of additional periodic synchronization events.

8. The method of claim 1 wherein the flow characteristic determination is an average push volume per average time between pauses.

9. A method of fluid flow rate estimation of a pump comprising:
   detecting a periodic synchronization event, via inserted bubble tracking of a signal processor unit comprising a central processing unit and addressable memory, wherein the periodic synchronization event indicates at least one of: a present point in a push-pause cycle and a present range in a push-pause cycle;
   wherein the periodic synchronization event detecting comprises:
      detecting one or more pushes of a pump based on a time-interval and at least one of: a carriage position change, a carriage motion, and a fluid pressure change; and
      detecting one or more pauses of a pump based on time-interval, a threshold, and at least one of: a carriage position change, a carriage motion, and a fluid pressure change; and
   synchronizing a flow characteristic determination based on the periodic synchronization event,
   wherein synchronizing the flow characteristic determination further comprises:
      collecting flow data during at least one of: the detected one or more pushes of the pump and the detected one or more pauses of the pump; and
      adding the collected flow data to an average value only when a detected pause of the pump is followed by a detected push of the pump.

10. The method of claim 9 wherein the fluid flow rate is estimated to within a 1% error in two to ten push-pause cycles of the pump.

11. A method of fluid flow rate estimation of a pump comprising:
    detecting a periodic synchronization event, via inserted bubble tracking of a signal processor unit comprising a central processing unit and addressable memory, wherein the periodic synchronization event indicates at least one of: a present point in a push-pause cycle and a present range in a push-pause cycle; and
    synchronizing a flow characteristic determination based on the periodic synchronization event,
    wherein the periodic synchronization event detecting comprises:
       detecting one or more pushes of a pump based on a time-interval and at least one of: a carriage position change, a carriage motion, and a fluid pressure change; and
       detecting one or more pauses of a pump based on time-interval, a threshold, and at least one of: a carriage position change, a carriage motion, and a fluid pressure change;

wherein the inserted bubble tracking comprises:
  inserting a first bubble into the fluid flow;
  tracking, by the signal processor unit, a travel of at least one of: the leading edge of the inserted first bubble and the trailing edge of the inserted first bubble, the tracking based on received emission levels of a photo-detector output by a first photo-detector disposed on a controlled, translatable carriage, wherein the translatable carriage is configured to move in a translational motion relative to the fluid flow;
  inserting a second bubble into the fluid flow; and
  determining if the first inserted bubble is lost, wherein:
    if the first inserted bubble is lost, then returning the controlled, translatable carriage to a starting position, and
    if the first inserted bubble is not lost, then determining if the second inserted bubble is detected, wherein:
      if the second inserted bubble is not detected, then tracking the first inserted bubble, and
      if the second inserted bubble is detected, then tracking, by the signal processor unit, a travel of at least one of: a leading edge of the inserted second bubble and a trailing edge of the inserted second bubble, the tracking based on received emission levels of the photo-detector output by the first photo-detector disposed on the controlled, translatable carriage.

12. The method of claim 11 wherein the fluid flow further comprises a U-shaped conduit comprising an outflow portion and an inflow portion.

13. The method of claim 12 further comprising:
  determining if the first inserted bubble is detected in the inflow portion of the fluid flow, wherein:
    if the first inserted bubble is detected in the inflow portion of the fluid flow, then tracking, by the signal processor unit, the travel of at least one of: the leading edge of the inserted first bubble in the inflow portion and the trailing edge of the inserted first bubble in the inflow portion, the tracking based on received emission levels of a photo-detector output by a second photo-detector disposed on the controlled, translatable carriage, and
    if the first inserted bubble is not detected in the inflow portion of the fluid flow, then tracking, by the signal processor unit, the travel of at least one of: the leading edge of the inserted second bubble in the outflow portion and the trailing edge of the inserted second bubble in the outflow portion, the tracking based on received emission levels of the photo-detector output by the first photo-detector disposed on a controlled, translatable carriage.

\* \* \* \* \*